(12) United States Patent
Flanagan et al.

(10) Patent No.: US 11,860,096 B2
(45) Date of Patent: Jan. 2, 2024

(54) EXTENDED SOLID ANGLE TURBIDITY SENSOR

(71) Applicant: YSI, INC., Yellow Springs, OH (US)

(72) Inventors: Kevin Flanagan, Yellow Springs, OH (US); Ronald Metzger, Clarksville, OH (US); Kyle Loges, Township, OH (US)

(73) Assignee: YSI, INC., Yellow Springs, OH (US)

( * ) Notice: Subject to any disclaimer, the term of this patent is extended or adjusted under 35 U.S.C. 154(b) by 185 days.

(21) Appl. No.: 17/324,385

(22) Filed: May 19, 2021

(65) Prior Publication Data

US 2021/0364430 A1 Nov. 25, 2021

Related U.S. Application Data

(60) Provisional application No. 63/028,723, filed on May 22, 2020, provisional application No. 63/028,013, (Continued)

(51) Int. Cl.
*G01N 21/53* (2006.01)
*G01N 21/64* (2006.01)
(Continued)

(52) U.S. Cl.
CPC ..... *G01N 21/6456* (2013.01); *G01N 21/4785* (2013.01); *G01N 21/532* (2013.01); (Continued)

(58) Field of Classification Search
CPC .......... G01N 21/6456; G01N 21/4785; G01N 21/532; G01N 21/64; G01N 21/82; (Continued)

(56) References Cited

U.S. PATENT DOCUMENTS 4,160,914 A * 7/1979 Wynn .................. G01N 21/49
250/237 R
5,059,811 A * 10/1991 King .................. G01N 21/4785
356/442
(Continued)

FOREIGN PATENT DOCUMENTS

WO 2016/095008 A1 6/2016
WO 2018/007786 A1 1/2018
(Continued)

OTHER PUBLICATIONS

Xiong et al. "Broadband photodetectors based on enhanced photothermal effect of polymer encapsulated graphene film", Appl. Surf. Sc. Adv. 3 (2021).*

(Continued)

*Primary Examiner* — Mohamed K Amara
(74) *Attorney, Agent, or Firm* — Ware, Fressola, Maguire & Barber LLP (57) ABSTRACT

A turbidity sensor featuring a signal processor or processing module configured to: receive signaling containing information about light reflected off suspended matter in a liquid and sensed by a linear sensor array having rows and columns of optical elements; and determine corresponding signaling containing information about a concentration of turbidity of the liquid, based upon the signaling received.

16 Claims, 6 Drawing Sheets

Related U.S. Application Data filed on May 21, 2020, provisional application No. 63/027,587, filed on May 20, 2020.

(51) Int. Cl.
| | |
|---|---|
| *G01N 33/08* | (2006.01) |
| *G01N 21/47* | (2006.01) |
| *G01N 21/82* | (2006.01) |
| *H04N 25/46* | (2023.01) |

(52) U.S. Cl.
CPC ............ *G01N 21/64* (2013.01); *G01N 21/82* (2013.01); *G01N 33/08* (2013.01); *H04N 25/46* (2023.01); *G01N 2021/6473* (2013.01); *G01N 2021/6491* (2013.01); *G01N 2201/061* (2013.01); *G01N 2201/0633* (2013.01); *G01N 2201/0636* (2013.01); *G01N 2201/126* (2013.01); *G01N 2201/12761* (2013.01); *G01N 2201/12792* (2013.01)

(58) Field of Classification Search
CPC ........... G01N 33/18; G01N 2021/6473; G01N 2021/6491; G01N 2201/061; G01N 2201/0633; G01N 2201/0636; G01N 2201/126; G01N 2201/12761; G01N 2201/12792; G01N 2021/4709; G01N 21/53; H04N 25/46
See application file for complete search history.

(56) References Cited

U.S. PATENT DOCUMENTS

| | | | | |
|---|---|---|---|---|
| 5,436,476 | A * | 7/1995 | Hynecek | G11C 27/04 257/224 |
| 5,486,693 | A | 1/1996 | Achter et al. | |
| 6,070,093 | A * | 5/2000 | Oosta | A61B 5/1455 600/316 |
| 6,466,318 | B1 | 10/2002 | Agrawal et al. | |
| 6,573,991 | B1 * | 6/2003 | Debreczeny | G01N 15/0211 356/336 |
| 6,844,934 | B2 * | 1/2005 | Retzlaff | G01N 21/532 356/440 |
| 6,894,778 | B2 | 5/2005 | Palumbo et al. | |
| 7,046,347 | B1 * | 5/2006 | Amend | G01N 21/51 356/402 |
| 7,361,472 | B2 | 4/2008 | Yguerabide et al. | |
| 7,920,252 | B2 | 4/2011 | Hu | |
| 8,345,248 | B2 | 1/2013 | Hong et al. | |
| 8,603,772 | B2 | 12/2013 | Debreczeny et al. | |
| 8,654,319 | B2 | 2/2014 | Rao et al. | |
| 9,435,726 | B2 | 9/2016 | Smart et al. | |
| 9,696,192 | B2 | 7/2017 | Nyhart, Jr. | |
| 9,752,974 | B2 | 9/2017 | Debreczeny et al. | |
| 9,863,881 | B2 | 1/2018 | Sinfield et al. | |
| 10,036,703 | B1 * | 7/2018 | Ng | G01N 21/255 |
| 10,054,532 | B2 | 8/2018 | Debreczeny et al. | |
| 10,088,571 | B2 | 10/2018 | Vuorenkoski-Dalgleish et al. | |
| 10,150,680 | B1 * | 12/2018 | Kurani | G01N 33/18 |
| 2002/0017612 | A1 * | 2/2002 | Yu | H01L 51/4206 250/370.11 |
| 2003/0117623 | A1 * | 6/2003 | Tokhtuev | G01N 21/53 356/338 |
| 2004/0022677 | A1 * | 2/2004 | Wohlstadter | G01N 21/253 422/52 |
| 2004/0130716 | A1 * | 7/2004 | Couston | G01N 21/6456 356/318 |
| 2005/0219526 | A1 | 10/2005 | Peng | |
| 2007/0222980 | A1 * | 9/2007 | Palumbo | G01N 21/532 356/243.1 |
| 2007/0222984 | A1 * | 9/2007 | Palumbo | G01N 15/0227 356/338 |
| 2009/0027670 | A1 * | 1/2009 | Selker | G01N 21/51 356/338 |
| 2009/0230288 | A1 | 9/2009 | Blaesing | |
| 2010/0007879 | A1 * | 1/2010 | Mavliev | G01N 15/1459 356/336 |
| 2010/0233753 | A1 * | 9/2010 | Tsukii | G01N 21/645 356/442 |
| 2010/0288944 | A1 * | 11/2010 | Avdeef | G01N 21/0332 250/461.1 |
| 2010/0321046 | A1 * | 12/2010 | Randall | G01N 27/07 324/696 |
| 2011/0019194 | A1 * | 1/2011 | Muller | G01N 21/274 356/442 |
| 2011/0208031 | A1 * | 8/2011 | Wolfe | A61B 5/291 600/378 |
| 2011/0273710 | A1 * | 11/2011 | Dong | G01N 21/8507 356/338 |
| 2012/0044493 | A1 * | 2/2012 | Smart | G01N 21/49 356/336 |
| 2012/0064516 | A1 * | 3/2012 | Kajihara | B01L 3/50851 435/6.1 |
| 2012/0099098 | A1 * | 4/2012 | Webster | G01N 21/03 356/244 |
| 2012/0149005 | A1 * | 6/2012 | Kojima | B01L 7/52 435/286.1 |
| 2012/0223260 | A1 * | 9/2012 | Hansen | G01N 15/1459 250/576 |
| 2012/0287435 | A1 * | 11/2012 | Adams | G01N 15/1429 356/340 |
| 2013/0336567 | A1 * | 12/2013 | Chan | G01N 33/5094 382/133 |
| 2014/0177932 | A1 * | 6/2014 | Milne | G01N 21/8851 382/128 |
| 2014/0234984 | A1 * | 8/2014 | Juuti | G01N 21/532 436/172 |
| 2015/0276594 | A1 | 10/2015 | Johnson et al. | |
| 2016/0121009 | A1 * | 5/2016 | Farr | G02B 19/0095 250/492.1 |
| 2017/0074793 | A1 * | 3/2017 | Strickler | G02B 26/12 |
| 2017/0241893 | A1 | 8/2017 | Walls et al. | |
| 2017/0254752 | A1 * | 9/2017 | Palassis | G01N 21/59 |
| 2017/0276603 | A1 * | 9/2017 | Leggett | G01N 21/51 |
| 2017/0299511 | A1 * | 10/2017 | Palassis | G01J 3/28 |
| 2017/0307495 | A1 * | 10/2017 | Corbett | G01N 15/0211 |
| 2018/0128746 | A1 * | 5/2018 | Zhang | G01N 15/06 |
| 2018/0156730 | A1 * | 6/2018 | Flanagan | G01N 21/645 |
| 2018/0251713 | A1 | 9/2018 | Angelescu et al. | |
| 2019/0041320 | A1 | 2/2019 | Martinez-Carreras | |
| 2019/0063965 | A1 * | 2/2019 | Rojo | G01D 11/245 |
| 2019/0212256 | A1 * | 7/2019 | Joch | G01N 21/251 |
| 2019/0234863 | A1 * | 8/2019 | Diebold | G01N 15/1429 |
| 2019/0234873 | A1 * | 8/2019 | Riding | G01N 21/276 |
| 2020/0033648 | A1 * | 1/2020 | Chamanzar | G02F 1/125 |
| 2020/0200686 | A1 * | 6/2020 | Reed | G01N 21/53 |
| 2021/0181019 | A1 * | 6/2021 | Chang | A61B 5/4872 |
| 2021/0349082 | A1 * | 11/2021 | Straus | C12Q 1/20 |
| 2021/0364430 | A1 * | 11/2021 | Flanagan | G01N 21/82 |
| 2021/0364438 | A1 * | 11/2021 | Flanagan | G01N 21/6456 |
| 2022/0413166 | A1 * | 12/2022 | Saccomanno | A23L 3/28 |

FOREIGN PATENT DOCUMENTS

| | | |
|---|---|---|
| WO | 2018/089935 A1 | 5/2018 |
| WO | 2018/233198 A1 | 12/2018 |

OTHER PUBLICATIONS

"Turbidity and Total Suspended Solids Measurement Methods"; www.fondriest.com (Accessed Jun. 10, 2019) https://www.fondriest.com/environmentalmeasurements/measurements/measuring-water-quality/turbidity-sensorsmeters-and-methods; 2019; whole document.

"Aqua Troll 600 Multiparameter Sonde" in-situ.com; https://web.archive.org/web/20151109045641/https://insitu.com/products/water-quality-testing-equipment/aqua-troll-600-multiparameter-sonde; Nov. 9, 2015; whole document.

(56) References Cited

OTHER PUBLICATIONS

"Submersible Electrochemical Sensors" pubs.acs.org; https://pubs.acs.org/doi/full/10.1021/acs.analchem.7b05299; Mar. 8, 2018; whole document.
English translation of WO 2018/233198A1.

* cited by examiner

Figure 1

Apparatus, including a turbidity sensor, 10

A quasi-collimated light source 20 configured to provide quasi-collimated light Lc on a liquid having suspended matter.

A linear sensor array 30 configured to sense light Lr reflected off the suspended matter in the liquid and provide signaling containing information about light Lr reflected of the suspended matter.

A photodiode 30a configured at an end of the linear array

Signal processor 40 configured at least to:

receive the signaling; and/or determine corresponding signaling containing information about a concentration of parameter (e.g., such as turbidity) of the liquid, based upon the signaling received.

Other signal processor circuits, circuitry, or components 50 that do not form part of the underlying invention, e.g., including input/output modules/modems, one or more memory modules (e.g., RAM, ROM, etc.), data, address and control busing architecture, etc.

Figure 2A: Turbidity sensor 10

| | | | | | | | | | |
|---|---|---|---|---|---|---|---|---|---|
| (r1, c1) | (r1, c2) | (r1, c3) | (r1, c4) | (r1, c5) | (r1, c6) | (r1, c7) | (r1, c8) | | (r1, cn) |
| (r2, c1) | (r2, c2) | (r2, c3) | (r2, c4) | (r2, c5) | (r2, c6) | (r2, c7) | (r2, c8) | | (r2, cn) |
| (r3, c1) | (r3, c2) | (r3, c3) | (r3, c4) | (r3, c5) | (r3, c6) | (r3, c7) | (r3, c8) | | (r3, cn) |
| | | | | ... | | | | | |
| (rn, c1) | (rn, c2) | (rn, c3) | (rn, c4) | (rn, c5) | (rn, c6) | (rn, c7) | (rn, c8) | | (rn, cn) |

30

Figure 2B: Linear sensor array

Figure 3

Figure 4: Side view of captured backscattered radiation

Figure 5: Sensitivity Comparison

Figure 6A: Three-dimensional rendering of solid angle capture for an idealized long-cylinder shell geometry Figure 6B: Three-dimensional rendering of solid angle capture for an idealized long-cylinder shell geometry

EXTENDED SOLID ANGLE TURBIDITY SENSOR

CROSS-REFERENCE TO RELATED APPLICATIONS

This application claims benefit to provisional patent application Ser. No. 63/027,587 (911-023.9-1-1/N-YSI-0045US01), filed 20 May 2020; 63/028,013 (911-023.010-1-1/N-YSI-0046US02), filed 21 May 2020, and 63/028,723 (911-023.011-1-1/N-YSI-0047US02), filed 22 May 2020, which are all incorporated by reference in its entirety.

BACKGROUND OF THE INVENTION

1. Field of Invention

This invention relates to a sensor for measuring the quality of water; and more particularly, to a turbidity sensor for measuring the quality of water.

2. Description of Related Art

Traditional turbidity sensing techniques suffer from poor sensitivity (especially field-deployable sensors) stemming from poor/inefficient capture of scattered signal (solid angle). Existing turbidity sensors typically employ a single excitation light source and a single, or point-like emission receiver, utilizing a photosensitive element. Regardless of the particular photosensitive element or excitation light source used, the current turbidity sensors known in the art are not opto-mechanically configured for efficient capture of solid angle resulting in compromised limit of detection for turbidity.

Figure 1:
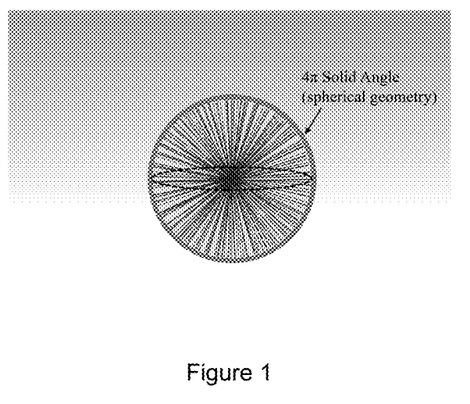
FIG. 1 is a diagram of a spatial distribution of scattered radiation of a single turbid particle that is approximated by a sphere, resulting in $4\pi$ [steradians] solid angle of scattered radiation that is known in the art.

The difficulty with measuring scattering-based signals is the spatial/directional nature of randomly scattered optical radiation. Consider for the moment the excitation of a single turbid particle. For typical environmental water quality monitoring conditions, the spatial distribution of scattered radiation of a single turbid particle is well approximated by a sphere, resulting in $4\pi$ [steradians] solid angle of scattered radiation (See FIG. 1). To optimally capture such a turbidity signal would require a photosensitive area that closely matches the radiation pattern, i.e., a photosensitive area in the shape of a spherical shell. See FIG. 1. In view of this, there is a need in the art for a better turbidity sensor.

Moreover, and by way of example, PCT/US2008/059575, filed 7 Apr. 2008, entitled "System and method for high-throughput turbidity measurements," discloses techniques for turbidity measurements using a spatial-gradient method. The turbidity measurement system includes a sample assembly that contains a plurality of samples, a light source that illuminates the sample assembly, and a light detection system that includes a two-dimensional light-sensitive array. The light-sensitive array is simultaneously exposed to light transmitted through each of the samples in the sample assembly. The exposure is analyzed to determine a mean transmitted light intensity for each sample and to calculate a turbidity value for each sample based on its mean transmitted light intensity. Multiple exposures may be taken during a measurement period so as to obtain time-resolved turbidity measurements of the samples. The temperature of the samples may be varied during the measurement period so as to measure turbidity as a function of temperature.

SUMMARY OF THE INVENTION

In summary, the present invention aims to greatly enhance the captured solid angle thereby significantly enhancing the sensitivity of turbidity measurements.

The sensor under consideration incorporates (insofar that is practicable in a field-rugged sensor) many of the features exhibited in the idealized long-cylinder geometry. The present invention employs a linear photodiode array (the proposed approach is not limited to photodiode technology, e.g., a linear CCD or CMOS array could be used as well). The linear array allows ample room for biofouling counter measures such as motorized wiping. Additionally, linear sensor arrays are currently available as relatively inexpensive commercial-of-the-shelf (COTS) components.

The key to this invention pertains specifically to the opto-mechanical configuration which utilizes a wide, linear array along the length of the quasi-collimated light source for enhanced signal capture. Additionally, the design allows for the capture of back scattered radiation—all in a single embodiment The present design is compatible with non-intensity-based determinations of turbidity. These measurements are spatially dependent, the main idea being that an optical signal will undergo an attenuation across the linear array, following Beer's law, thereby creating a "spatial gradient". This spatial gradient contains information regarding the concentration of the turbidity.

The non-intensity-based measurement is immune to "drift" of the excitation source. In other words, the spatial gradient is unaffected by moderate changes in the intensity of the excitation source, e.g., LED intensity degradation through the course of use, or a change in optical power due to thermal effects.

The "spatial gradient" method according to the present invention enables real-time, inner filter effect (IFE) correction, which greatly enhances high-concentration sensing range. (In comparison, a known technique of inner filter correction involves post processing via lab analysis after a field deployment.)

Additionally, the "spatial gradient" method according to the present invention also allows for certain types of interference correction not achievable with amplitude-based techniques known in the art.

The above "spatial gradient" method requires that each optical element in the array be individually addressable. However, there is a possible variant of the design that involves connecting all of the linear array elements in a parallel configuration which would preclude the possibility of individual addressability. However, such a design variant could be modified to include a transmission photodiode (located at the end of the array, opposite of the source) which would restore the sensor's ability to perform drift correction and IFE correction.

SPECIFIC EMBODIMENTS

According to some embodiments, the present invention may include, or take the form of, apparatus featuring a signal processor or processing module configured to:

receive signaling containing information about light reflected off suspended matter in a liquid and sensed by a linear sensor array having rows and columns of optical elements; and determine corresponding signaling containing information about a concentration of parameter of the liquid, based upon the signaling received The apparatus may include one or more of the following additional features:

The parameter may include turbidity of the liquid.

The apparatus may include the linear sensor array.

The linear sensor array may include a linear photodiode array.

The linear sensor array may include a linear CCD array.

The linear sensor array may include a linear CMOS array.

The linear sensor array may include a closed cylinder sensor array having a three-dimensional cylindrical array of the rows and columns of the optical elements.

The apparatus may be a turbidity sensor.

The apparatus may include a quasi-collimated light source having a length and being configured to provide the light, including quasi-collimated light, along a corresponding length of the linear sensor array.

The signal processor or processing module may be configured to determine the parameter based upon an attenuation of an optical signal sensed across the linear sensor array.

The linear sensor array may include a two-dimensional array of optical elements that are individually addressable.

The signal processor or processing module may be configured to determine the turbidity based upon a spatial gradient of an optical signal sensed across the linear sensor array that contains information about the concentration of the turbidity.

The optical elements may be individually addressable by the signal processor or processing module.

Either the rows or the columns of the optical elements may be connected in parallel and addressable by the signal processor or processing module; the apparatus may include a transmission photodiode located at an end of the linear sensor array, opposite the light source, configured to respond to the light reflected off the suspended matter and provide transmission photodiode signaling containing information about the same; and the signal processor or processing module may be configured to receive the photodiode signaling and correct the corresponding signaling for drift or the inner filter effect.

According to some embodiments, the present invention may include a turbidity sensor featuring a quasi-collimated light source, a linear sensor array and a signal processor or processing module. The quasi-collimated light source has a length and may be configured to provide quasi-collimated light to a liquid sample. The linear sensor array may include rows and columns of optical elements and be configured to sense light reflected off suspended matter in the liquid sample along the length of the quasi-collimated light source and provide signaling containing information about the light reflected off the suspended matter. The signal processor or processing module may be configured to:
  receive the signaling; and
  determine corresponding signaling containing information about a concentration of turbidity of the liquid, based upon the signaling received The turbidity sensor may also include one or more of the features set forth above.

The Method

According to some embodiments, the present invention may include a method, featuring:
  receiving, with a signal processor or processing module, signaling containing information about light reflected off suspended matter in a liquid and sensed by a linear sensor array having rows and columns of optical elements; and
  determining, with the signal processor or processing module, corresponding signaling containing information about a concentration of a parameter of the liquid, based upon the signaling received The method may also include one or more of the features set forth above.

Computer-readable Storage Medium

According to some embodiments of the present invention, the present invention may also take the form of a computer-readable storage medium having computer-executable components for performing the steps of the aforementioned method. The computer-readable storage medium may also include one or more of the features set forth above.

Advantages

The present invention offers distinct advantages over the current known techniques in the prior art, as follows:
1) The optimized capture of solid angle greatly enhances the signal sensitivity thereby significantly enhancing the minimum limit of detection for turbidity. A linear sensor array provides a much larger overall active area to capture scattered rays. More importantly, the active area is larger in the dimension that matters most, along the direction of the quasi-collimated excitation source. Additionally, a wider linear array is preferred over a thin one for reasons stated above, increased active area. However, there is a limit of diminishing return regarding the width, i.e., an array width that does not roughly match the diameter of the excitation beam appears non-ideal.
2) The present invention enables measurement of backscattered radiation (in addition to the radially emitted side scatter)—all in a single sensing embodiment.
3) The distance between the quasi-columnar excitation source to the linear sensor array was minimized as this also enhances sensitivity in addition to sensing range.

BRIEF DESCRIPTION OF THE DRAWING

The drawing, which are not necessarily drawn to scale, includes FIGS. 1-6B, as follows.

To reduce clutter in the drawing, each Figure in the drawing does not necessarily include every reference label for every element shown therein.

DETAILED DESCRIPTION OF BEST MODE OF THE INVENTION

Figure 2A:
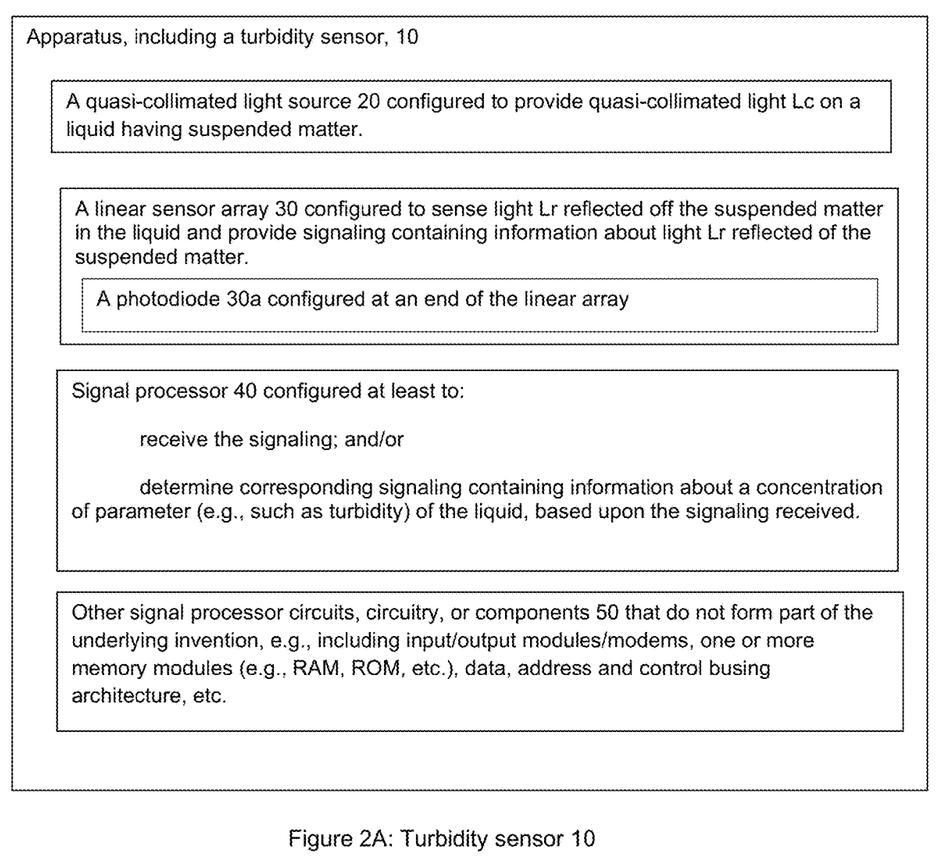
FIG. 2A is a block diagram of apparatus, including a turbidity sensor, according to some embodiments of the present invention.

FIG. 2 shows apparatus 10, including a turbidity sensor, according to the present invention having a quasi-collimated light source 20, a linear sensor array 30, and a signal processor or processing module 40.

Figure 2B:
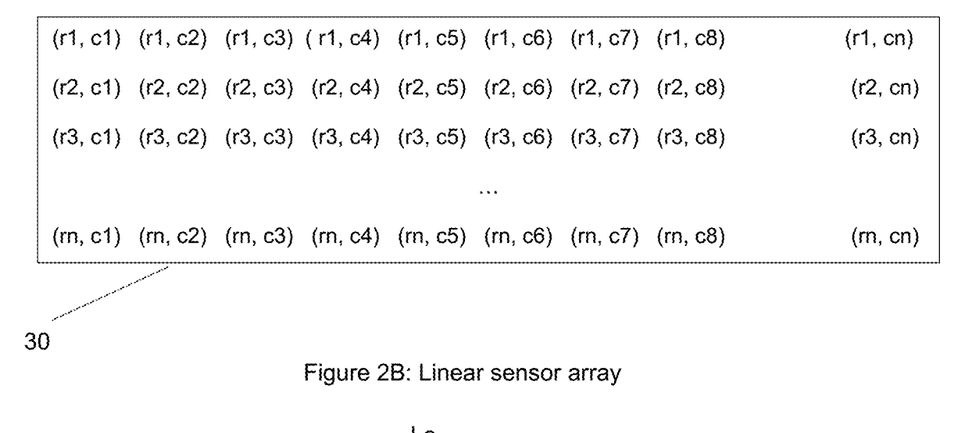
FIG. 2B is a block diagram of a linear sensor array having rows and columns of optical elements, according to some embodiments of the present invention.

The signal processor or processing module 40 may be configured to
- receive signaling containing information about light Lr reflected off suspended matter in a liquid and sensed by the linear sensor array 30 having rows and columns of optical elements (r1, c1; r1, c2; r1, c3; r1, c4; r1, c5; r1, c6; r1, c7; r1, c8; . . . ; r1, cn; r2, c1; r2, c2; r2, c3; r2, c4; r2, c5; r2, c6; r2, c7; r2, c8; . . . ; r2, cn; r3, c1; r3, c2; r3, c3; r3, c4; r3, c5; r3, c6; r3, c7; r3, c8; . . . ; r3, cn; . . . ; rn, c1; rn, c2; rn, c3; rn, c4; rn, c5; rn, c6; rn, c7; rn, c8; . . . ; rn, cn); and
- determine corresponding signaling containing information about a concentration of parameter of the liquid, based upon the signaling received

The Parameter

By way of example, the parameter may include the concentration of turbidity in the liquid, and the apparatus may be, or take the form of, a turbidity sensor. However, the scope of the invention is not intended to be limited to any particular type or kind of parameter being sensed in a liquid either now known or later developed in the future.

The Linear Sensor Array 30

By way of example, the apparatus 10 may include the linear sensor array 30, e.g., such as a linear photodiode array, a linear charge-coupled device (CCD) array, a linear CMOS array. In particular, the linear sensor array 30 may include a two-dimensional array of rows and columns of optical elements, e.g., like that shown in FIG. 2B, that are individually addressable. Linear sensor arrays are known in the art, and the scope of the invention is not intended to be limited to any particular type or kind thereof either now known or later developed in the future.

By way of example, linear sensors arrays are disclosed in the following U.S. Pat. Nos. 9,020,202; 8,022,349; 7,956,341; 7,040,538; 5,252,818; and 4,193,057, which are all hereby incorporated by reference.

Figure 3:
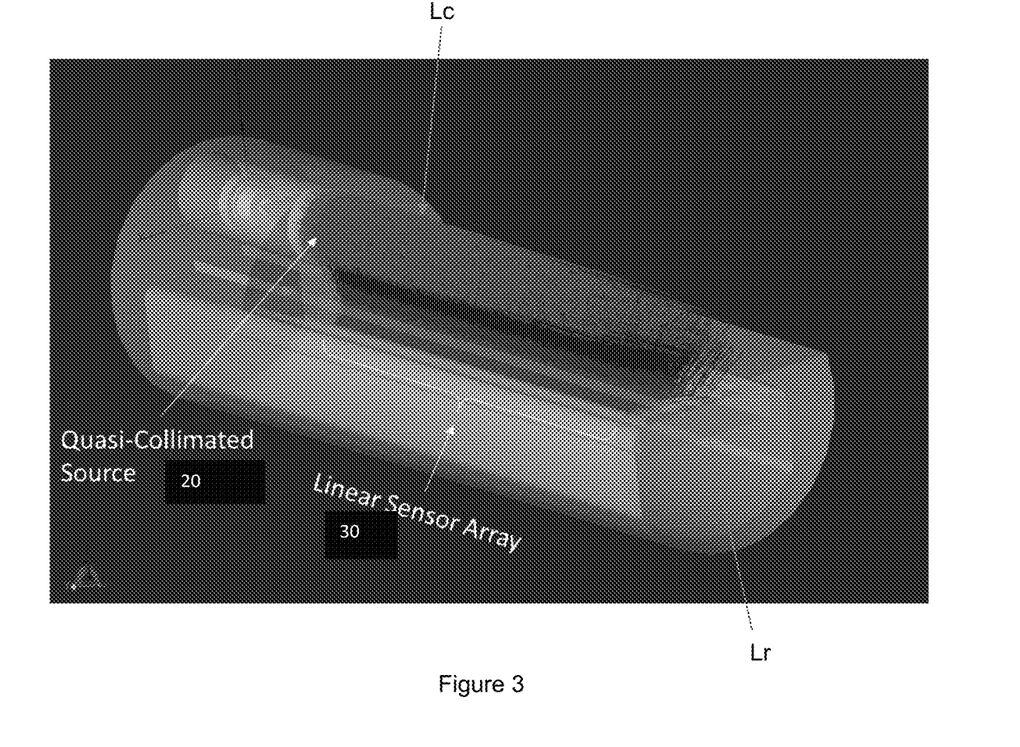
FIG. 3 is a three dimension perspective view of a quasi-collimated light source that provides a quasi-collimated light in relation to a linear sensor array, according to some embodiments of the present invention.
Figure 4:
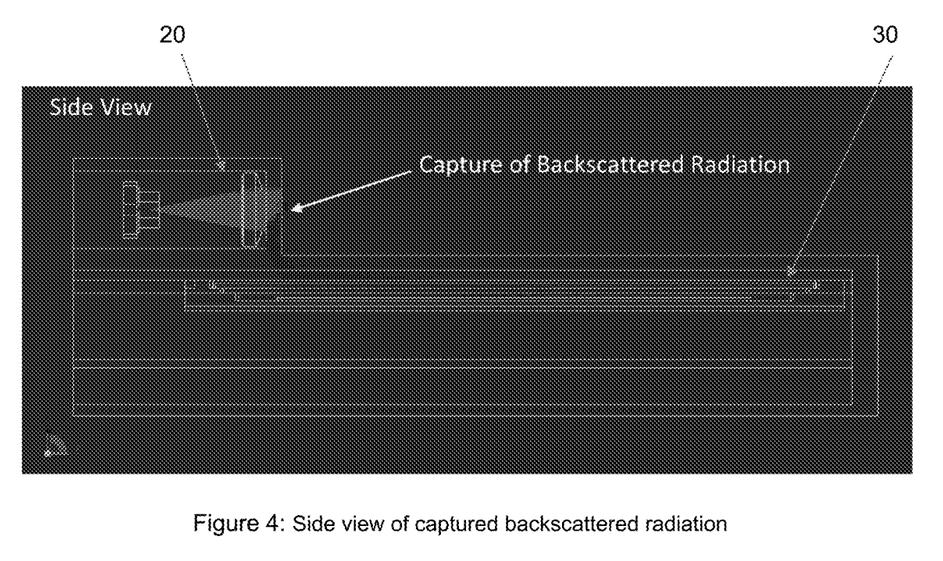
FIG. 4 is a side view of that shown in FIG. 3 showing captured backscatter radiation by the linear sensor array, according to some embodiments of the present invention.
Figure 5:
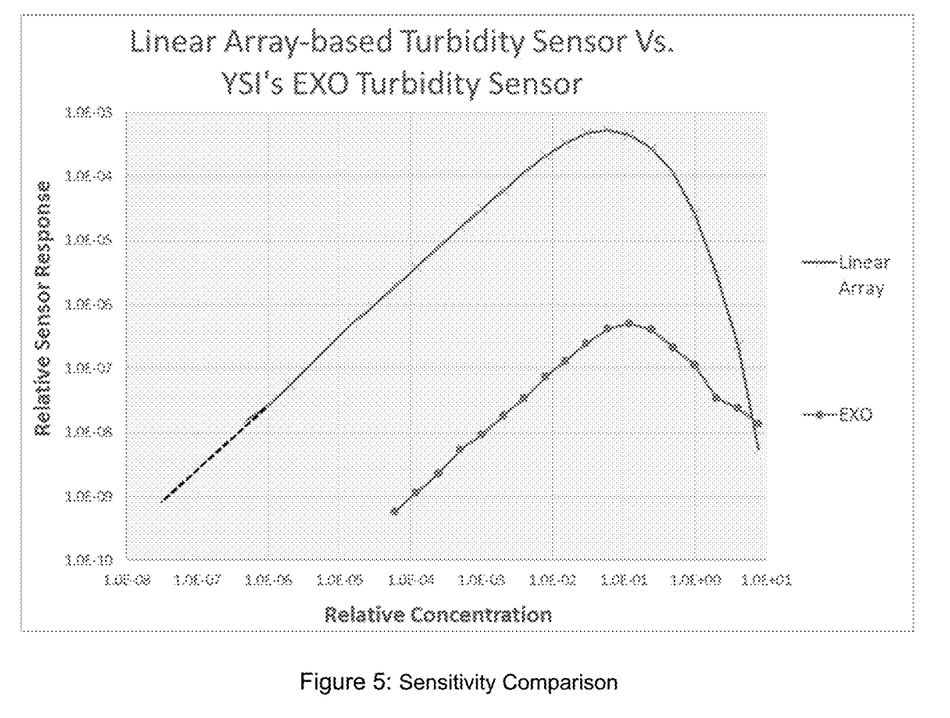
FIG. 5 is a graph of relative sensor response versus relative concentration, e.g., showing a sensitivity comparison of the assignee's contemporary EXO turbidity sensor (solid line with dots) vs. the linear array turbidity sensor (solid line). Note that the graph shows simulated data based on a physical model of the design according to the present invention.

FIGS. 3 and 4

By way of example, the apparatus 10 may include the source 20 configured to provide the light Lc, including quasi-collimated light, along a corresponding length of the linear sensor array 30, e.g., as shown in FIGS. 2 and 3, e.g., through a liquid sample arranged in relation to the light source 20 and the linear sensor array 30 so as to reflect the light Lr off suspended matter in the liquid sample being monitored or tested onto the linear sensor array 30. For example, the light Lr may be reflected radially (FIG. 3) and backwards (FIG. 4), i.e., backscattered reflected light or radiation.

As a person skilled in the art would appreciate, quasi-collimated light sources are known in the art, and the scope of the invention is not intended to be limited to any particular type or kind thereof either now known or later developed in the future.

FIG. 4 shows captured backscatter radiation by the linear sensor array 30, where backscattered radiation is understood to be light reflected of the suspended matter in the liquid sample that travels backwards, consistent with that shown.

The Signal Processor or Processing Module 40

By way of example, the signal processor or processing module 40 may be configured to determine the parameter, including turbidity, based upon an attenuation of an optical signal sensed across the linear sensor array, including its length and width. Techniques for sensing the attenuation of the optical signal, e.g., in relation to the concentration of turbidity in the liquid, are known in the art, and the scope of the invention is not intended to be limited to any particular type or kind thereof either now known or later developed in the future.

By way of example, the signal processor or processing module 40 may be configured to determine the concentration of turbidity based upon a spatial gradient of the optical signal sensed across the linear sensor array. As a person skilled in the art would appreciate, techniques for determining the concentration of turbidity in a liquid based upon a spatial gradient of an optical signal are known in the art, e.g., consistent with that set forth herein re PCT/US2008/059575, which is hereby incorporated by reference in its entirety, and the scope of the invention is not intended to be limited to any particular type or kind of technique either now known or later developed in the future.

In an alternative embodiment, either the rows or the columns of the optical elements may be connected in parallel and addressable by the signal processor or processing module 40; the apparatus 10 may include a transmission photodiode 30a located at an end of the linear sensor array 30, opposite the light source 20, configured to respond to the light L reflected off the suspended matter and provide transmission photodiode signaling containing information about the same; and the signal processor or processing module 40 may be configured to receive the photodiode signaling and correct the corresponding signaling for drift or the inner filter effect.

Implementation of Signal Processing Functionality

By way of example, the functionality of the signal processor or processing module 40 may be implemented using hardware, software, firmware, or a combination thereof. In a typical software implementation, the signal processor 40 would include one or more microprocessor-based architectures having, e.g., at least one signal processor or microprocessor. One skilled in the art would be able to program with suitable program code such a microcontroller-based, or microprocessor-based, implementation to perform the signal processing functionality disclosed herein without undue experimentation.

The scope of the invention is not intended to be limited to any particular implementation using technology either now known or later developed in the future. The scope of the invention is intended to include implementing the functionality of the signal processor(s) as stand-alone processor, signal processor, or signal processor module, as well as separate processor or processor modules, as well as some combination thereof.

By way of example, the apparatus 10 may also include, e.g., other signal processor circuits or components generally indicated 50, including random access memory or memory module (RAM) and/or read only memory (ROM), input/output devices and control, and data and address buses connecting the same, and/or at least one input processor and at least one output processor, e.g., which would be appreciate by one skilled in the art.

By way of further example, the signal processor may include, or take the form of, some combination of a signal processor and at least one memory including a computer program code, where the signal processor and at least one memory are configured to cause the system to implement the functionality of the present invention, e.g., to respond to signaling received and to determine the corresponding signaling, based upon the signaling received.

Figure 6A:
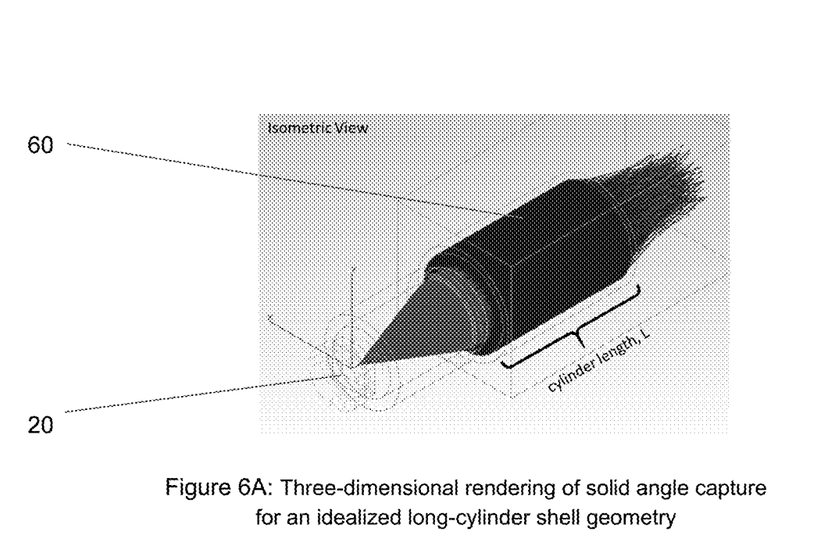
FIG. 6A is an isometric view showing of a three-dimensional rendering of solid angle capture for an idealized long-cylinder shell geometry, e.g., such as a 3-D cylindrical linear sensor array, according to the present invention.
Figure 6B:
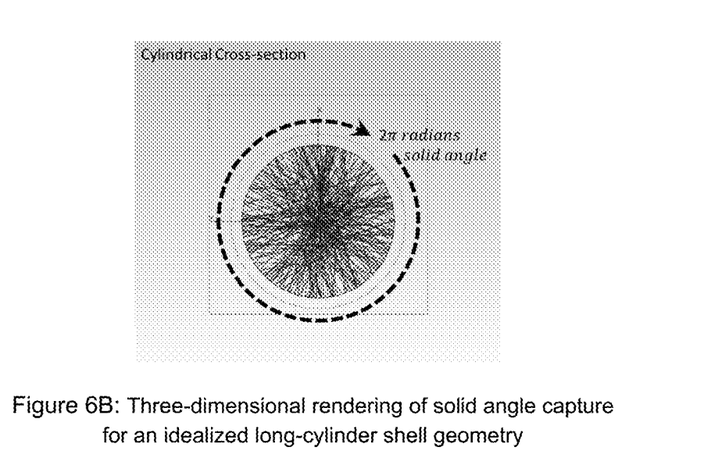
FIG. 6B is a cross-sectional view showing of the idealized long-cylinder shell geometry, e.g., such as the 3-D cylindrical linear sensor array.

FIGS. 6A and 6B: The 3D Cylindrical Linear Sensor Array 60

By way of example, the apparatus 10 may include a closed cylinder sensor array 60 having a three-dimensional cylindrical array of the rows and columns of the optical elements and a length L, e.g., as shown in FIG. 6A.

In FIG. 6A, the 3-D cylindrical linear sensor array 32 configured to capture light reflected off the suspended matter in the liquid along its length L and 360 degrees radially about its longitudinal axis.

As a person skilled in the art would appreciate, common/practical light sources including LEDs, laser diodes or broad-band lamps are often configured to provide a columnar or quasi-columnar optical radiation pattern for which the ideal photosensitive area takes the shape of a long, cylindrical shell, capturing rays perpendicular to the excitation column. According to the inventor at the time of this patent application filing, there are no commercially available "closed-cylinder" sensor arrays.

Inner Filter Effect (IFE)

As a person skilled in the art would appreciate, the IFE is a fluorescence spectroscopy phenomenon, e.g., where there is a decrease in fluorescence emission seen in concentrated solutions due to the absorption of exciting light by the fluorophore that is close to the incident beam and which significantly diminishes light that reaches the sample further away from it.

As a person skilled in the art would appreciate, techniques for correcting for the IFE are known in the art, and the scope of the invention is not intended to be limited to any particular type or kind thereof either now known or later developed in the future.

Applications

The present invention has applications, e.g., in the basic parameter of water quality monitoring for freshwater applications (e.g., where turbidity is one of the "big five"), as well as drinking water monitoring.

THE SCOPE OF THE INVENTION

While the invention has been described with reference to exemplary embodiments, it will be understood by those skilled in the art that various changes may be made, and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A turbidity sensor comprising:
    a quasi-collimated light source having a length and being configured to provide quasi-collimated light to a liquid sample that causes gradient light to scatter and reflect transversely off suspended matter in the liquid sample along the length of the collimated light source;
    a linear sensor array having rows and columns of optical elements and configured to sense the gradient light scattered and reflected transversely off the suspended matter in the liquid sample along the length of the collimated light source and provide signaling containing information about the gradient light sensed; and
    a signal processor or processing module configured to:
        receive the signaling; and
        determine corresponding signaling containing information about a concentration of turbidity of the liquid sample that spatially depends on an attenuation of the gradient light sensed across the linear sensor array and along the length of the collimated light source, based upon the signaling received.

2. A turbidity sensor according to claim 1, wherein the linear sensor array comprises a linear photodiode array, a linear CCD array, or a linear CMOS array.

3. A turbidity sensor according to claim 1, wherein the linear sensor array comprises a closed cylinder sensor array having a three-dimensional cylindrical array of the rows and columns of the optical elements.

4. A turbidity sensor according to claim 1, wherein the signal processor or processing module is configured to determine the parameter based upon an attenuation of an optical signal sensed across the linear sensor array, including along the length and width of the linear sensor array.

5. A turbidity sensor according to claim 1, wherein the signal processor or processing module is configured to determine the turbidity based upon a spatial gradient of an optical signal sensed across the linear sensor array that contains information about the concentration of the turbidity.

6. A turbidity sensor according to claim 1, wherein the linear sensor array comprises a two-dimensional array of the optical elements that are individually addressable.

7. A turbidity sensor according to claim 6, wherein the optical elements are individually addressable by the signal processor or processing module.

8. A turbidity sensor according to claim 6, wherein
    either the rows or the columns of the optical elements are connected in parallel and addressable by the signal processor or processing module;
    the turbidity sensor includes a transmission photodiode located at an end of the linear sensor array, opposite the light source, configured to respond to the light reflected off the suspended matter and provide transmission photodiode signaling containing information about the same; and
    the signal processor or processing module is configured to receive the photodiode signaling and correct the corresponding signaling for drift or an inner filter effect.

9. A method for determining a concentration of turbidity, comprising:
- providing quasi-collimated light to a liquid sample with a quasi-collimated light source having a length that causes gradient light to scatter and reflect transversely off suspended matter in the liquid sample along the length of the collimated light source;
- sensing the gradient light scattered and reflected transversely off the suspended matter in the liquid sample along the length of the collimated light source with a linear sensor array having rows and columns of optical elements;
- providing signaling containing information about the gradient light sensed;
- receiving, with a signal processor or processing module, the signaling; and
- determining, with the signal processor or processing module, corresponding signaling containing information about a concentration of a parameter of the liquid sample that spatially depends on an attenuation of the gradient light sensed across the linear sensor array and along the length of the collimated light source, based upon the signaling received.

10. A method according to claim 9, wherein the method comprises configuring the linear sensor array as a linear photodiode array, a linear CCD array, or a linear CMOS array.

11. A method according to claim 9, wherein the method comprises configuring the linear sensor array as a closed cylinder sensor array having a three-dimensional cylindrical array of the rows and columns of the optical elements.

12. A method according to claim 9, wherein the method comprises determining with the signal processor or processing module the parameter based upon an attenuation of an optical signal sensed across the linear sensor array, including along the length and width of the linear sensor array.

13. A method according to claim 9, wherein the method comprises determining with the signal processor or processing module the turbidity based upon a spatial gradient of an optical signal sensed across the linear sensor array that contains information about the concentration of the turbidity.

14. A method according to claim 9, wherein the method comprises configuring the linear sensor array as a two-dimensional array of the optical elements that are individually addressable.

15. A method according to claim 14, wherein the method comprises configuring the signal processor or processing module and the optical elements so that the optical elements are individually addressable by the signal processor or processing module.

16. A method according to claim 14, wherein the method comprises
- connecting either the rows or the columns of the optical elements in parallel and addressable by the signal processor or processing module;
- locating a transmission photodiode at an end of the linear sensor array, opposite the light source to respond to the light reflected off the suspended matter and provide transmission photodiode signaling containing information about the same; and
- configuring the signal processor or processing module to receive the photodiode signaling and correct the corresponding signaling for drift or an inner filter effect.

* * * * *